(12) United States Patent
Green et al.

(10) Patent No.: US 10,040,425 B2
(45) Date of Patent: Aug. 7, 2018

(54) SYSTEM FOR DETECTING WINDSHIELD WIPER NOISE AND RELATED METHODS

(71) Applicant: FORD GLOBAL TECHNOLOGIES, LLC, Dearborn, MI (US)

(72) Inventors: Alfred Green, Belleville, MI (US); David Karl Bidner, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 28 days.

(21) Appl. No.: 15/348,235

(22) Filed: Nov. 10, 2016

(65) Prior Publication Data
US 2018/0126955 A1    May 10, 2018

(51) Int. Cl.
*B60S 1/08* (2006.01)
*G01N 29/44* (2006.01)

(52) U.S. Cl.
CPC ........ *B60S 1/0822* (2013.01); *G01N 29/4463* (2013.01)

(58) Field of Classification Search
CPC .......................... B60S 1/0822; G01N 29/4463
USPC ............................................................ 701/36
See application file for complete search history.

(56) References Cited

U.S. PATENT DOCUMENTS

| 5,119,002 A * | 6/1992 | Kato ..................... B60S 1/0818 318/444 |
| 5,254,916 A | 10/1993 | Hopkins |
| 5,642,026 A | 6/1997 | McCann et al. |
| 6,057,660 A | 5/2000 | Meier et al. |
| 7,194,781 B1 | 3/2007 | Orjela |
| 8,285,437 B2 | 10/2012 | Kubota et al. |
| 9,365,188 B1 * | 6/2016 | Penilla ................ B60R 25/2018 |
| 2010/0204987 A1 * | 8/2010 | Miyauchi ................ G10L 15/25 704/233 |
| 2013/0185078 A1 * | 7/2013 | Tzirkel-Hancock .... G10L 15/22 704/275 |
| 2015/0048771 A1 * | 2/2015 | Caillaud ................... B60S 1/08 318/519 |

(Continued)

FOREIGN PATENT DOCUMENTS

| DE | 3935807 A1 | 5/1991 |
| DE | 19955874 A1 | 5/2001 |
| DE | 10254684 A1 | 6/2004 |

(Continued)

OTHER PUBLICATIONS

English Machine Translation of DE102009048687A1.

(Continued)

*Primary Examiner* — Yazan A Soofi
(74) *Attorney, Agent, or Firm* — Jason Rogers; King & Schickli, PLLC

(57) ABSTRACT

A system for detecting noise generated by a windshield wiper on a vehicle including a cabin is provided. The system includes a detector for detecting noise generated by the windshield wiper. A processor is provided for generating a signal based on the noise detected by the detector. A controller may also receive the signal and regulate the operation of the windshield wiper, including by adaptive control based on a vehicle operator's desired setting of a speed of the wiper in an intermittent mode of operation. The signal may also be used to notify a service provider of the need for servicing the windshield wiper. Related methods are also disclosed.

20 Claims, 3 Drawing Sheets

(56) References Cited

U.S. PATENT DOCUMENTS

2016/0250997 A1* 9/2016 Toda .................. B60S 1/0807
                                                     701/49

FOREIGN PATENT DOCUMENTS

| DE | 102009048687 A1 | 4/2011 |
| EP | 2730470 A1 | 5/2014 |
| JP | 200507902 A | 6/2000 |
| JP | 2010052470 A | 3/2010 |
| KR | 19970040176 A | 7/1997 |
| WO | 9614225 A1 | 5/1996 |
| WO | 20010381474 A1 | 5/2001 |

OTHER PUBLICATIONS

English Machine Translation of DE10254684A1.
English Machine Translation of DE19955874A1.
English Machine Translation of JP200507902A.
English Machine Translation of JP2010052470A.
English Machine Translation of KR19970040176A.
English Machine Translation of WO200010381474A1.
English Machine Translation of DE3935807A1.

* cited by examiner

SYSTEM FOR DETECTING WINDSHIELD WIPER NOISE AND RELATED METHODS

TECHNICAL FIELD

This document relates generally to the motor vehicle field and, more particularly, to a system for detecting windshield wiper noise and related methods.

BACKGROUND

Windshield wipers may audibly squeak or "chatter" as a result of a "slip stick" interaction between the wiper blade and the windshield. Chattering is effected by the amount of surface friction and water lubrication, as well as the condition and angle of the wiper blades, and often results in complaints by vehicle operators. Typically, the operator will turn the wipers off or reduce their frequency to reduce the chatter, but this manual intervention does not really resolve the underlying issue if it pertains to the quality or condition of the wiper blades. Since the chatter may be an intermittent phenomenon, vehicle operators often forget to address the issue later with their service provider during maintenance visits, and are reminded of the problem only when it recurs later, which creates an endless cycle of inattention to the problem.

Thus, a need is identified for detecting the presence of windshield wiper chatter and taking further action to resolve it, desirably without the need for intervention by the vehicle operator.

SUMMARY

In accordance with the purposes and benefits described herein, a system for detecting noise generated by a windshield wiper on a vehicle including a cabin is provided. The system comprises a detector for detecting noise generated by the windshield wiper. A processor is provided for generating a signal based on the noise detected by the detector, which may be a microphone associated with the vehicle cabin.

In one embodiment, the system includes a motor for moving the windshield wiper. A controller is also provided for controlling the motor based on the signal. The controller may be adapted for regulating a speed of the motor based on the signal.

The processor may generate the signal by filtering a noise signal from the detector. This may be done by removing an audio output signal corresponding to audio output from a speaker associated with the cabin. The processor may also generate the signal taking into account a position of the windshield wiper.

The processor may be adapted to generate a code indicative of a need for replacing the windshield wiper. A memory may be provided for storing the code. Alternatively or additionally, a transmitter may be provided for transmitting the code to a vehicle service provider.

In accordance with a further aspect of the disclosure, a system for detecting noise generated by of a windshield wiper on a vehicle including a cabin is provided. The system comprises a motor for moving the windshield wiper, a microphone for detecting noise associated with the operation of the windshield wiper, and a controller for controlling the motor based on the detected noise. A processor may be adapted to generate a code indicative of a need for replacing the windshield wiper based on the detected noise. The system may further include one or more of a memory for storing the code and a transmitter for transmitting the code to a vehicle service provider.

A further aspect of the disclosure pertains to a method for detecting chatter of a windshield wiper on a vehicle including a cabin. The method comprises detecting noise associated with the operation of the windshield wiper and generating a signal based on the noise detected by the detector. The method may further include the step of filtering the signal, and also controlling movement of the windshield wiper based on the signal.

Still further, the method may include the step of indicating a need for replacing the windshield wiper. The indicating step may comprise storing a code in a memory associated with the vehicle. The indicating step may further comprise transmitting a code to a vehicle service provider.

In the following description, there are shown and described several preferred embodiments of a system for detecting windshield wiper noise and related methods. As it should be realized, the arrangement is capable of other, different embodiments and its several details are capable of modification in various, obvious aspects all without departing from the system for detecting windshield wiper noise and related methods, as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the system for detecting windshield wiper noise and related methods and, together with the description, serve to explain certain principles thereof. In the drawing figures.

Reference will now be made in detail to the present preferred embodiments of a system for detecting windshield wiper noise and related methods, examples of which are illustrated in the accompanying drawing figures.

DETAILED DESCRIPTION

Figure 1:
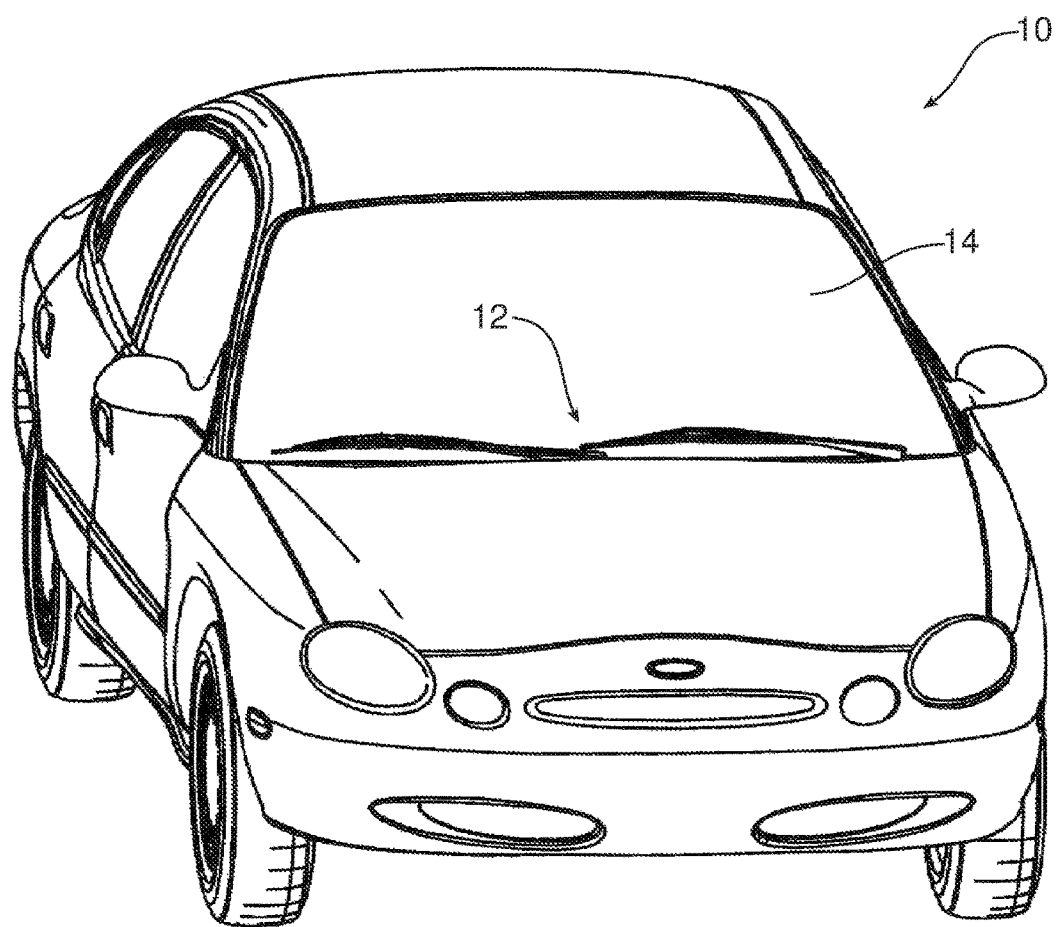
FIG. 1 is a front perspective view of a motor vehicle including a windshield with wipers.
Figure 2:
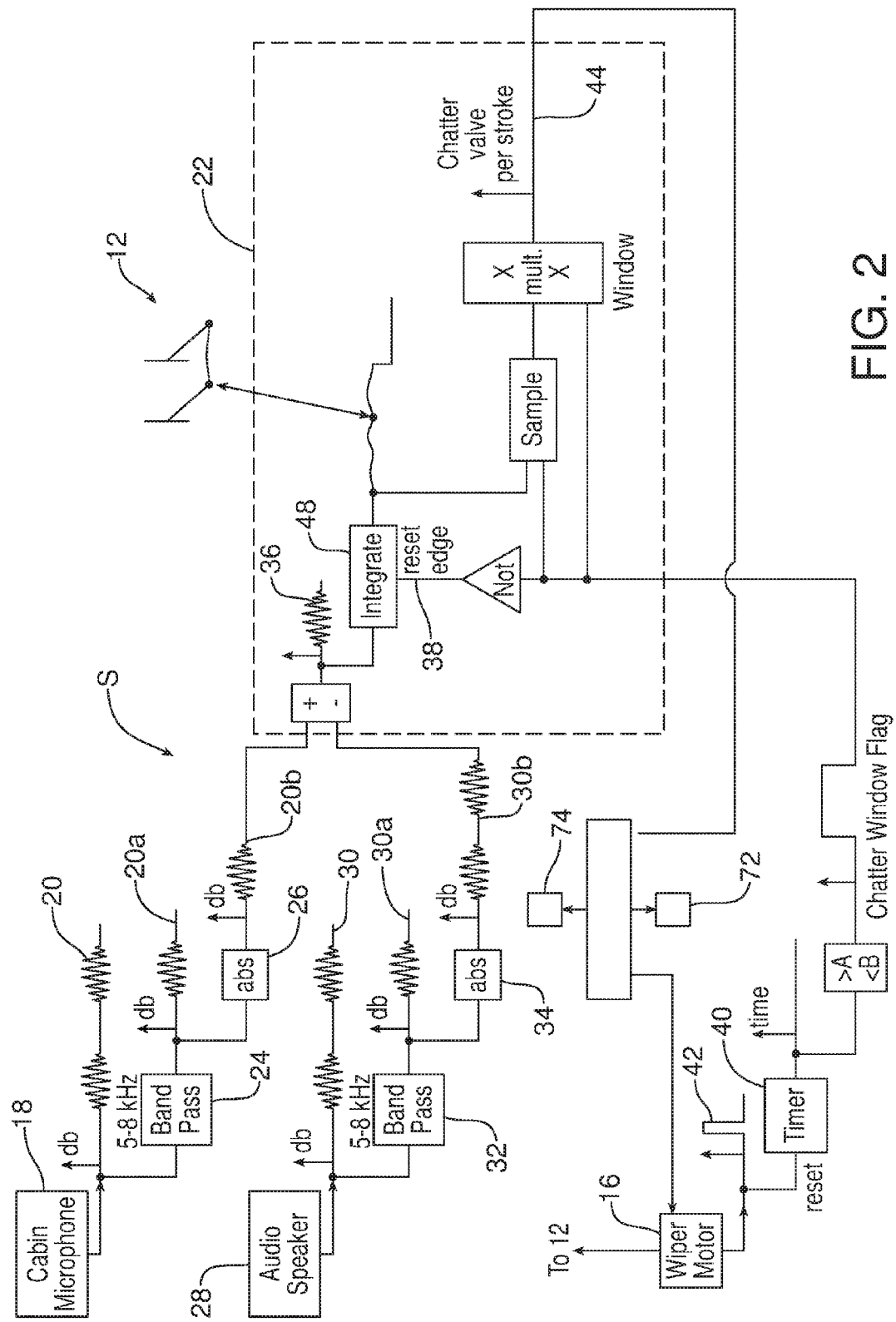
FIG. 2 is a schematic diagram illustrating one embodiment of a system for detecting windshield wiper noise.

Reference is now made to FIG. 1, which illustrate a vehicle 10 including one or more wipers 12 for wiping a windshield 14. The wiper(s) may be caused to move to and fro to sweep the windshield 14 as a result of selective actuation by a wiper motor 16, which may be controlled using a control (not shown) in the vehicle cabin. As is customary, the control may include an intermittent setting that causes the wiper(s) 12 to operate based on a user-selected period, which may be desirable when the rain is light or intermittent.

According to one aspect of the disclosure, a system S is provided for detecting the presence of noise resulting from the operation of the wiper(s) 12, such as the result of vibrations resulting from traversing the windshield 14. In the illustrated embodiment, the system S includes a detector for detecting the noise, such as a microphone 18. The microphone 18 may be located in the vehicle cabin near the windshield 14 in a manner that simulates the capturing of the noise by the ear(s) of the vehicle operator.

Upon receiving the sound energy from the noise, the microphone 18 generates a signal 20 representative of the noise resulting from windshield wiper(s) 12 during operation. This signal 20 may be used by a processor 22 to generate a further signal based on the detected noise, which can be used in connection with the wiper motor 16 to regulate the operation of the wipers 12 (such as by reducing the period in order to attempt to abate the noise). In one embodiment, the signal 20 is filtered, such as by using a band pass filter 24 having a pre-determined range (5-8 kHz in one embodiment) to generate a filtered signal 20*a*. The absolute value 26 of this filtered signal 20*b* is then taken to generate a modified signal 20*b* representative of the contribution of the chatter to ambient noise.

To account for any noise generated by an audio speaker 28 delivering sound energy to the cabin, the sound signal 30 provided to it is similarly filtered, such as by a similar band pass filter 32, to generate a filtered audio signal 30*a*. The absolute value 34 of this filtered signal 30*a* is then taken to generate a modified signal 30*b* representative of the contribution of the sound energy from the audio speaker 28 to noise in the same pre-determined range. The processor 22 may receive the signals 20*b*, 30*b* as indicated, and subtract out the signal 30*b* corresponding to the audio contribution from speaker 28, thus creating a chatter noise signal 36 reflective of the noise generated from chatter caused by the wiper(s) 12.

This signal 36 may then be integrated with a signal 38 representative of the position of the wiper(s) in order to get a chatter value corresponding to each wiper stroke. In one embodiment, this involves calculating a wiper motor flag indicator when the wiper stroke is in the central part of the stroke (not the ends of stroke reversals), and also when the motor 16 is determined to be in a low speed setting as a result of intermittent operation. A timer 40 is set when the cycle start pulse 42 occurs, and a flag is set at a start and end of the wiper stroke.

The chatter noise signal 36 may then be correlated with the wiper stroke position to create a signal 44 indicative of a chatter value per stroke. This may be done by multiplying the signal 36 by the wiper stroke position and integrating 46 the value per stroke. This signal 44 may then be used to control the wiper operation and/or provide notification of the need for wiper adjustment or replacement, as outlined further in the following description.

Figure 3:
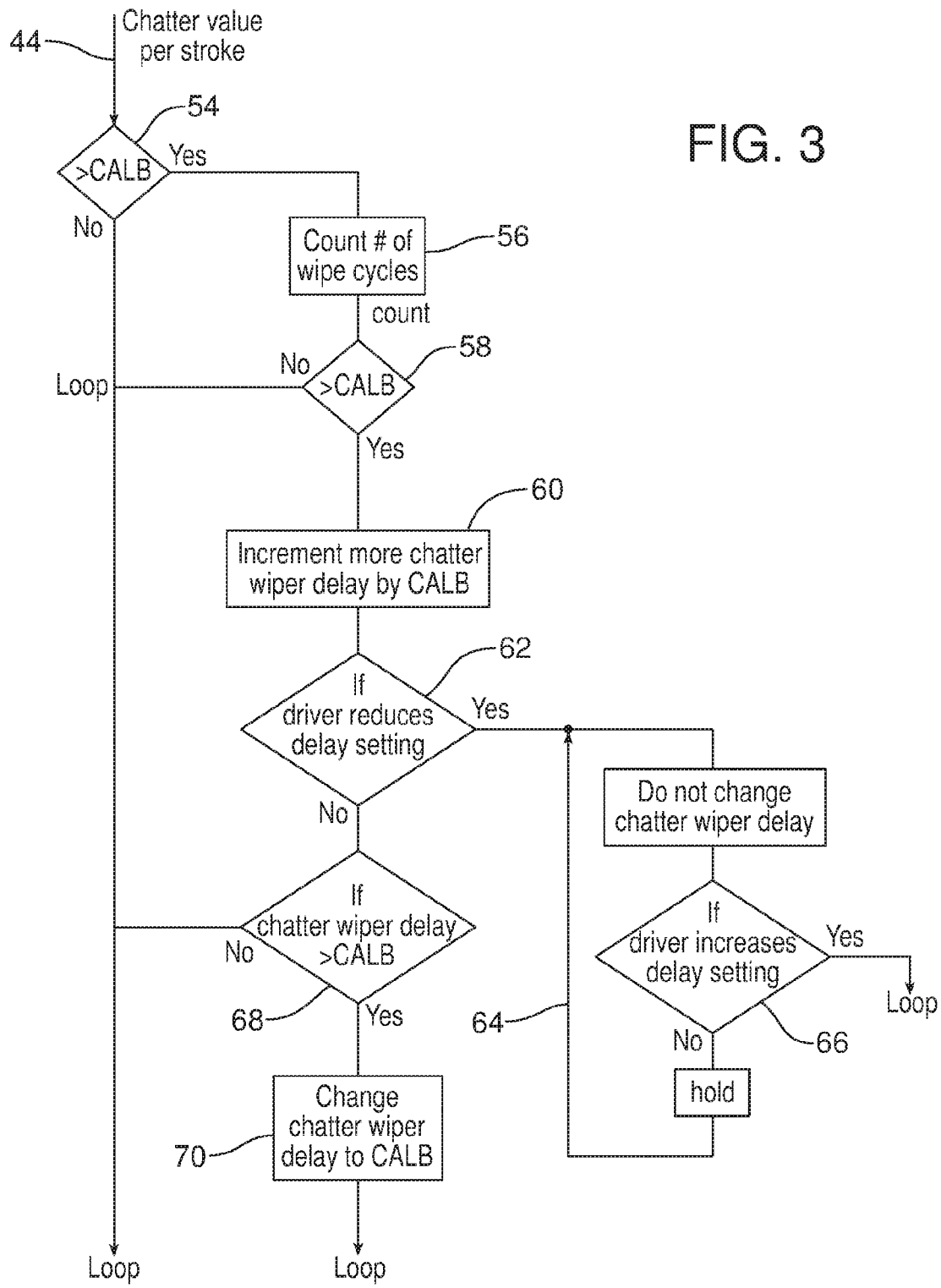
FIG. 3 is a flow chart illustrating a possible implementation of an automated control process for controlling the windshield wiper operation based on a detected level of noise and the vehicle operator's desired wiper settings.

In one aspect of the disclosure, the signal 44 may be provided to a controller 52 for controlling the wiper motor 16. The control may be as simple as simply causing the motor 16 to reduce the frequency of the wiper stroke. Alternatively, this control may involve an adaptive control measure, which seeks to avoid annoying the vehicle operator as a result of any change made to the wiper stroke as a result of detected chatter or squeaking. In the example shown in FIG. 3, the control may takes steps after every completed wiper stroke to determine if the wiper chatter value per stroke signal 44 is greater than a calibrated threshold value, as indicated at box 54. If so, then chatter is present, and the number of strokes that chatter is continuously present may be counted, as indicated at box 56. If the number of strokes that chatter is continuously present is greater than a calibrated threshold value, as indicated at box 58, the controller 52 may control the motor 16 to increase the delay time between intermittent strokes by a calibrated amount, as indicated at box 60. If the operator decreases the amount of delay (increase frequency) of the wiper motor 16, as indicated at box 62, then a hold situation arises and no changes to the chatter delay portion of the delay period are made, as indicated by sub-loop 64. If on the other hand the operator increases the delay (decrease frequency), as indicated at box 66, then the hold is abandoned and the process re-commences. If the setting is not reduced, but the chatter delay is greater than a calibration clip level, as indicated at box 68, then the delay is set to correspond to the calibration clip level, as indicated at box 70.

According to a further aspect of the disclosure, the controller 52 may also be adapted to indicate a need for ameliorative action. This may be achieved by storing a code in a memory 72, which may be generated as a result of no automatic adjustment being made (as a result of operator override) despite the presence of chatter, of if the automatic adjustment is ineffective to reduce the level of chatter. The code can then be read by a service provider later during a routine checkup or maintenance to know that the windshield wipers 12 are in need of attention. Additionally or alternatively, a transmitter 74 may be used to transmit a signal wirelessly to a service provider (such as a dealer who sold the vehicle to the operator) so that the wiper(s) 12 may be given suitable attention during a subsequent visit.

In summary, numerous benefits are provided by providing a vehicle 10 with a system S for detecting windshield wiper chatter. The presence of chatter may be automatically determined and used to regulate the operation of the wiper(s) 12, such as by using a controller 52 to control the wipers based on a signal 44 indicative of an amount of noise (chatter value per wiper stroke). The settings of the vehicle operator may also be taken into account, such as by holding on making adjustments when the operator increases the wiper frequency, but decreasing the frequency otherwise in an effort to reduce the amount of chatter. The system S may also be adapted to notify a service provider of the presence of chatter during operation of the vehicle prior to a maintenance visit, either by storing a code or transmitting a signal. Overall, the system S may reliably reduce the incidence of chatter without intervention by the vehicle operator.

The foregoing description has been presented for purposes of illustration. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A system for detecting noise generated by a windshield wiper on a vehicle including a cabin, comprising:
   a detector for detecting noise generated by the windshield wiper; and
   a processor for generating a signal for controlling the windshield wiper based on the noise detected by the detector.

2. The system of claim 1, further including:
   a motor for moving the windshield wiper; and
   a controller for controlling the motor based on the signal.

3. The system of claim 2, wherein the controller is adapted for regulating a speed of the motor based on the signal.

4. The system of claim 2, wherein the processor generates the signal by filtering a noise signal from the detector.

5. The system of claim 4, wherein the processor generates the signal by removing an audio output signal corresponding to audio output from a speaker associated with the cabin.

6. The system of claim 1, wherein the detector comprises a microphone associated with the cabin.

7. The system of claim 1, wherein the processor generates the signal taking into account a position of the windshield wiper.

8. The system of claim 1, wherein the processor is adapted to generate a code indicative of a need for replacing the windshield wiper.

9. The system of claim 8, further including a memory for storing the code.

10. The system of claim 8, further including a transmitter for transmitting the code to a vehicle service provider.

11. A system for detecting noise generated by of a windshield wiper on a vehicle including a cabin, comprising:
   a motor for moving the windshield wiper;
   a microphone for detecting noise from the windshield wiper; and
   a controller for controlling the motor based on the detected noise.

12. The system of claim 11, further including a processor adapted to generate a code indicative of a need for replacing the windshield wiper based on the detected noise.

13. The system of claim 12, further including a memory for storing the code.

14. The system of claim 12, further including a transmitter for transmitting the code to a vehicle service provider.

15. A method for detecting noise from a windshield wiper on a vehicle including a cabin, comprising:
   detecting noise associated with the operation of the windshield wiper; and
   generating a signal for controlling the windshield wiper based on the detected noise.

16. The method of claim 15, further including the step of filtering the signal.

17. The method of claim 15, further including the step of controlling movement of the windshield wiper based on the signal.

18. The method of claim 15, further including the step of indicating a need for replacing the windshield wiper.

19. The method of claim 18, wherein the indicating step comprises storing a code in a memory associated with the vehicle.

20. The method of claim 18, wherein the indicating step comprises transmitting a code to a vehicle service provider.

* * * * *